United States Patent [19]

Johnson et al.

[11] Patent Number: 4,632,121
[45] Date of Patent: Dec. 30, 1986

[54] SAFETY MEDICAL CABLE ASSEMBLY WITH CONNECTORS

[75] Inventors: Robert E. Johnson, Irvine; Philip H. Booker, III, El Toro, both of Calif.

[73] Assignee: Tronomed, Inc., Irvine, Calif.

[21] Appl. No.: 777,213

[22] Filed: Sep. 18, 1985

[51] Int. Cl.$^4$ .......................... A61B 5/04; H01R 11/00
[52] U.S. Cl. .................................. 128/639; 128/640; 128/783; 339/28; 339/75 R; 339/76; 339/186 R; 339/60 R
[58] Field of Search .......... 339/186 R, 186 M, 252 R, 339/252 S, 256 R, 256 S, 91 R, 94 R, 94 M, 75 R, 75 M, 28, 76, 77, 79, 66 M, 60 R, 60 C, 60 M, 253 R, 253 L, 253 F, 253 S; 128/640, 641

[56] References Cited

U.S. PATENT DOCUMENTS

| | | | |
|---|---|---|---|
| 2,190,230 | 8/1938 | Cole | 339/76 |
| 2,225,728 | 1/1939 | Weidenman, Sr. | 339/91 R |
| 2,567,727 | 4/1949 | Quackenbush | 339/94 R |
| 2,748,359 | 1/1952 | Swan | 339/28 |
| 3,029,820 | 7/1959 | Franklin | 128/640 |
| 3,085,577 | 6/1961 | Berman et al. | 128/641 |
| 4,490,005 | 12/1984 | Hovey | 128/641 |

FOREIGN PATENT DOCUMENTS 2243825 3/1974 Fed. Rep. of Germany ... 339/186 M

OTHER PUBLICATIONS

Instructions for Tronomed Dura-Lock Cable.

*Primary Examiner*—Kyle L. Howell
*Assistant Examiner*—Randy Citrin
*Attorney, Agent, or Firm*—Price, Gess & Ubell

[57] ABSTRACT

A safety medical cable assembly and terminal connector is provided including a first cable unit with a plug for connection to the monitor and a first connector unit connected to a flexible electrical conduit. A second cable unit having a second connector unit with a terminal pin for connection to the socket of a transducer is also interconnected with a flexible cable. The connector units can have a plurality of recesses and terminal pins mounted in a cantilevered arrangement from the bottom of the recess for interconnecting with a housing designed to fit within the recess. The terminal pins are shrouded from outside contact and preferably having a tubular configuration with an integral locking rim of a larger diameter. The terminal bores for receiving terminal pins includes an annular locking ring of a greater wear characteristic than the housing material of the connector units for receiving the locking rim on the terminal pin in a snap fitting action.

14 Claims, 13 Drawing Figures

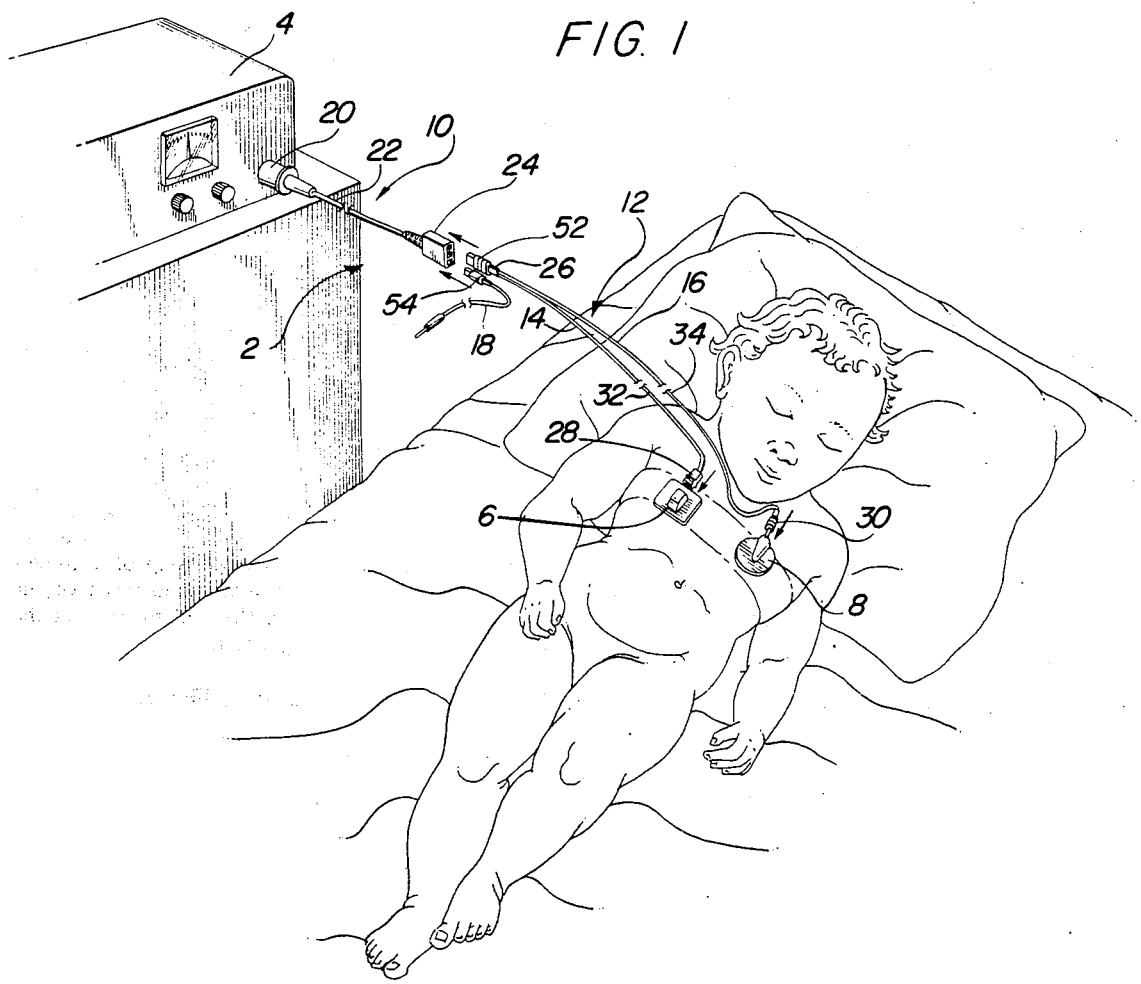
FIG. 1
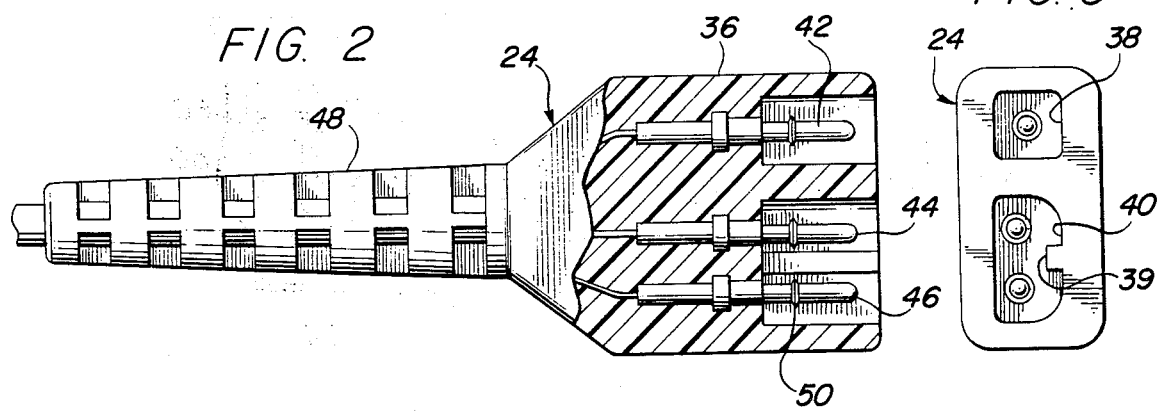
FIG. 2
FIG. 3

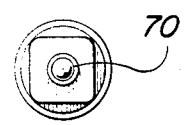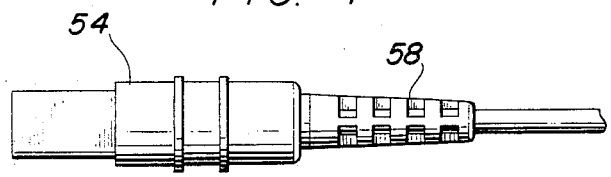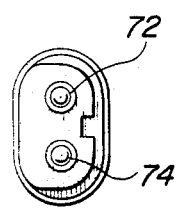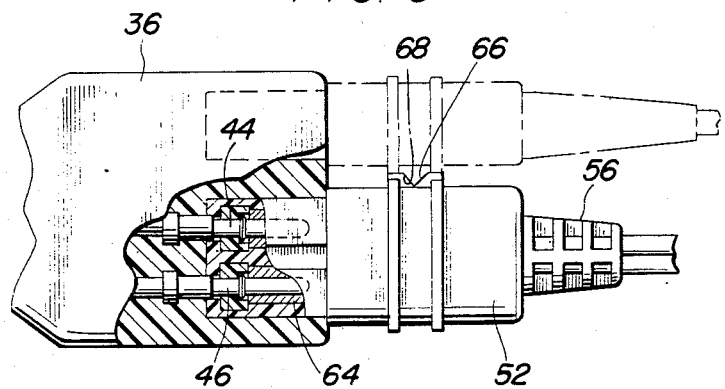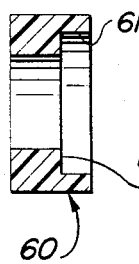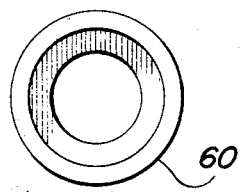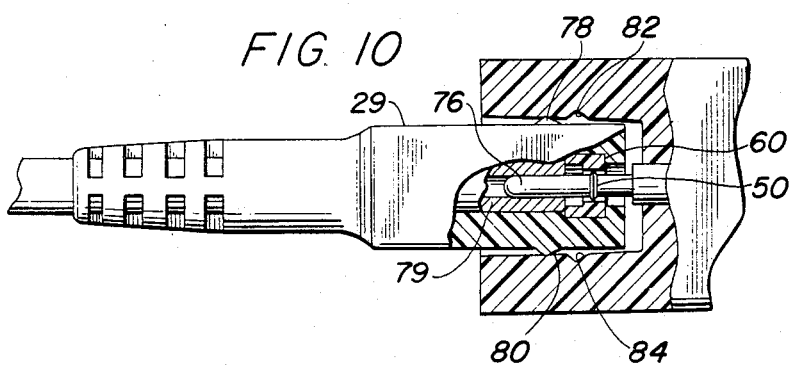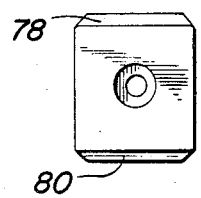

4,632,121

SAFETY MEDICAL CABLE ASSEMBLY WITH CONNECTORS

BACKGROUND OF THE INVENTION

1. Field of the Invention

The present invention relates to a medical connector and lead wire cable assembly and more particularly, to an improved connector and lead cable assembly for interconnecting a monitor with a transducer, such as a medical electrode, secured to a human body.

2. Description Of The Prior Art

In order to determine the electrical phenomena arising from physiological functioning of a patent, such as apnea monitoring of an infant or an electrocardiographic monitoring of a patient, it is necessary to electrically interconnect the patient with transducers or electrodes contacting the skin of a patient with a monitoring instrument, such as an electrocardiographic device. The interconnecting cable and connector assembly must be capable of coupling the electrical impulses from the transducers on the patient's body with relatively permanent connections that are noise free. Frequently, a first electrode cable lead is provided at one end with electrode terminal clips for interconnection with the transducers or electrodes on the patient's skin. The cable lead can have a plurality of terminal pins at the other end that can be color coded for connection to a connector plug mounted on a second cable lead that is attached by a terminal clip to a monitor. An example of just an electrical connector and terminal clip for attachment to an electrode assembly can be seen in U.S. Pat. No. 4,390,223.

Although the terminal pins can be color coded for matching with the indicia on the connector plug, it is still possible to mount the wrong terminal pin in the wrong terminal bore. Additionally the first electrode cable assembly is usually attached to the patient and the free exposed terminal pins can erroneously establish electrical contact with an inappropriate power source. This can be a particular safety problem in home apnea monitoring systems where other siblings can have access to the child who is being monitored. Thus, there is a need in the prior art to provide an improved, relatively inexpensive, safe medical cable assembly with connectors that can be fastened securely to ensure the proper electrical connection while minimizing any risk to the patient if the electrode lead cable assembly connector is left exposed.

SUMMARY OF THE INVENTION

The present invention provides an improved electrical cable system and terminal connectors for use in a monitoring medical system that can monitor the physiological functions of a patient. The electrical cable system comprises a first cable unit that can be connected directly to the monitor and includes an intermediate first connector unit that is interconnected with a monitor plug or socket through a flexible electrical conduit. A second cable unit that can be connected to a transducer such as a medical electrode on the patient also includes a second intermediate connector unit that is interconnected with a transducer connector through a second flexible electrical conduit. One of the first and second intermediate connector units is provided with a nonconductive housing having at least one recess and a plurality of terminal pins cantilevered within the recess and covered by an extended housing configuration. The other intermediate connector unit provides an insulating male housing configuration adapted to fit within the female recess that contains the male terminal pins, it further includes a pair of terminal bores or sockets for receiving and establishing electrical connection with the terminal pins. Since both the terminal pins and the terminal bores are mounted within and surrounded by insulated housing units, they are protected from erroneous contact with inappropriate power sources, and they are further designed to insure only a proper alignment interconnection of the intermediate connectors.

The terminal pins can be of a unique metal tubular configuration and can have an integral locking rim of a larger diameter than the remaining tubular portion for interfacing with a retaining locking rim or washer mounted within the entrance to the socket terminal bore and having a greater wear characteristic than the connector housing members. This locking interface will provide a snap fitting lock action to the interconnection of the intermediate connectors.

An additional connector cable assembly can be optionally provided, for example, to provide a ground connection, and its connector unit can interface with the transducer or electrode connector unit in such a manner as to be locked together when they are mounted within the common intermediate connector attached by the cable to the monitor.

Finally, both the transducer and the electrode connector can be designed with a locking shoulder on their housing units and locking rims on the internal terminal pin connectors to provide additional safety factors for preventing unwarranted electrical connections to the transducer attached to the patient's body.

Further objects and advantages of this invention will become apparent from a study of the following specification, claims and the attached drawings.

BRIEF DESCRIPTION OF THE DRAWINGS

FIG. 1 is a perspective view of the medical cable and connector assembly of the present invention attached to an infant;

FIG. 2 is a partial cross sectional view of a first intermediate connector unit;

FIG. 3 is an end view of the intermediate connector unit of FIG. 2;

FIG. 4 is a side view of a second intermediate connector unit;

FIG. 5 is an end view of the intermediate connector unit of FIG. 4;

FIG. 6 is a partial cross sectional view of a pair of intermediate connector units attached together;

FIG. 7 is an end view of the connector unit of FIG. 6;

FIG. 8 is a cross sectional view of an annular locking rim washer;

FIG. 9 is an end view of the annular locking rim washer;

FIG. 10 is a side view of an electrode connector unit;

FIG. 11 is an end view of the connector unit of FIG. 10;

DESCRIPTION OF THE PREFERRED EMBODIMENTS

Figure 12:
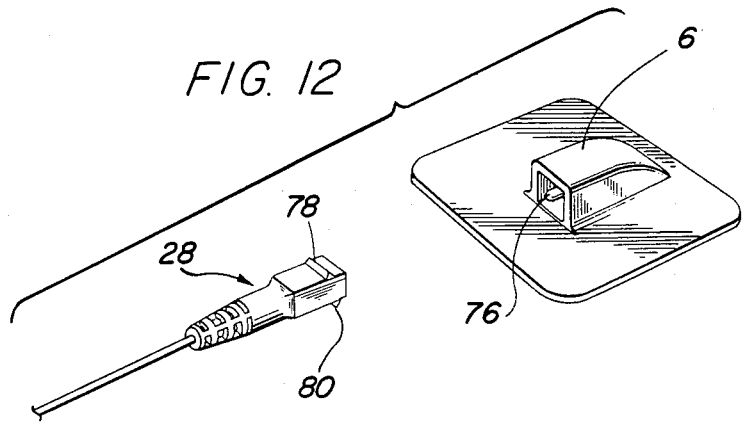
FIG. 12 is a perspective view of an electrode connector unit.

The following description is provided to enable any person skilled in the art of medical cable assemblies and electrode connector units to make and use the invention, and it sets forth the best modes contemplated by the inventors for carrying out their invention. Various modifications, however, will remain relatively apparent to those skilled in the above art, since the generic principles of the present invention are applied herein specifically to provide a relatively economical and easily manufactured detachable safety connector and cable assembly for medical use.

In manufacturing peripheral or accessory items in a medical monitoring system, such as the medical cable assembly and electrode connectors of the present invention, the manufacturer must first insure that he provides a product that is highly reliable and safe. Within these generic guidelines, the manufacturer must also be cost competitive to provide a successful product in the medical industry.

Referring to FIG. 1, a medical cable assembly 2 of the present invention is shown connected between a monitor 4 and electrodes 6 and 8 mounted on the body of an infant. The cable assembly 2 comprises a first cable unit 10 and a second cable unit 12. The second cable unit 12 can comprise one or more cable sets, for example, the second cable unit 12 includes a pair of cable sets 14 and 16 connected respectively to the electrodes 6 and 8, and a third cable set 18 for connection to ground.

A first cable unit 10 includes a plug 20 for electrical connection to a monitor 4. The plug 20 is interconnected with a first connector unit 24 by a flexible cable 22.

A second cable unit 12, such as the cable sets 14 and 16 which share a second connector unit 26 that is respectively connected with terminal sockets and jacks 28 and 30 via flexible cables 32 and 34 to the electrodes 6 and 8.

As shown in FIG. 2, the first connector unit 24 has an insulative plastic housing 36 with a plurality of recesses, such as recess 38 and 40. While two recesses are shown in the housing member 36, it should be appreciated that a number of separate recesses can be subjectively provided to meet the particular monitor requirements. Cantilevered from the bottom of the respective recesses are a plurality of terminal pins. Recess 38 has an axially positioned terminal pin 42 while recess 40 has terminal pins 44 and 46 cantilevered from the back of the recess. The terminal pins can be conventionally embedded within the insulative material of the housing member 36 during a molding process, as known in the art. The housing member 36 is preferably made of a relatively resilient plastic material such as a polyurethane or a polyvinyl, which can particularly accommodate a lead wire strain relief configuration 48 on the housing member 36 that facilitates the connection of the flexible cable 22 of the housing member 36. While the use of a soft resilient plastic material extends the life of the cable and provides a safety factor to prevent a break in the electrical conductivity of the cable, such material has limitations in providing an extensive wear life when used for securement or snap fitting between connectors. Frequently, detents or prongs are provided on a connector housing to secure the interconnection of the male plugs and female receptacle housing members.

The present inventors, recognizing the desirability of utilizing a relatively soft pliable plastic as the material for the connector housing 36 have designed a unique terminal pin configuration that includes an integral locking rim 50 that surrounds the tubular configuration of the terminal pin to facilitate a snap fitting or locking action with the companion female connector housings 52 and 54 of the second cable unit 12. The respective terminal pins 42, 44 and 46 are shown, respectively, with identical locking rims 50 in FIG. 2 and are formed from a conductive metal. Further, as can be seen in FIG. 2, the respective terminal pins 42, 44 and 46 are recessed from the exterior surface of the housing member 36 to prevent any unwarranted connection to an inappropriate source of power. Additionally, the perimeter configuration of the respective recesses 38 and 40 insure a predetermined matching of an insertion connector plug to thereby prevent any erroneous connection with a fail safe configuration additionally an alignment member 39 can interface with an alignment group 41 shown in FIG. 7.

Referring to FIGS. 4 through 7, the connector housing members 52 and 54 are disclosed and they are preferably formed from a similar resilient plastic material with appropriate strain relief connections 56 and 58 to their respective flexible cables. As can be seen respectively from FIGS. 5 and 7, the terminal bore housing configuration of both housings 52 and 54 have a complimentary exterior configuration to the perimeters of the recesses 38 and 40 of the connector housing member 36. These matching configurations insure a predetermined matching of the desired terminal pin and terminal bore. As can be readily appreciated, other configurations can be utilized to achieve the same purposes of the present invention.

Referring to FIG. 6, the terminal bore or socket housing 52 is shown in a cross sectional view to show the interface of the terminal pin locking rim 50 with an annular locking ring or washer 60 that can be seen in FIGS. 8 and 9. The ring 60 has a recessed annular shoulder 62 with a central bore whose inner diameter is smaller than the outer diameter of the locking rim 50. Extending from the annular shoulder 62 is a spacing rim 61 which defines an opening for receiving the locking rim of the terminal pin. The ring member 60 can be formed from an ABS plastic, such as a glass filled plastic sold under the trademark "Valox" by the General Electric Company. The annular ring 60 could be alternatively molded in place within the resilient housing material which forms the housing 52 adjacent the entrance of the terminal bore. A conductive receptacle member 64 provides the electrical contact with the terminal pin as known in the art.

Thus, as a result of this design feature of providing a locking rim 50 directly on the terminal pins along with the provision of a supporting or interfacing ring 60 having a central aperture for receiving the terminal pin, the present invention insures both a secure fastening of the respective connector units together, while appreciable extending the life of the connector units. Thus, the user of the present invention can expect an extended life to the medical cable assembly while still retaining the advantages of a relatively resilient plastic plug and receptacle configuration as expected in the prior art.

Referring to FIG. 6, an optional feature of the present invention can include a detent 66 and locking prong 68 mounted, respectively, on the housing members 52 and 54. Thus, when the ground wire plug housing 54 is inserted into the connector housing 36, the interface between the detent 66 and the locking prong 68 simply provides an additional secured point to maintain the stability of the united connectors. As can be readily appreciated detent 66 and the locking prong 68 could be inverted with the locking prong 68 positioned on the housing 52 and the detent 66 positioned on the housing member 54. Likewise, the position of the terminal pins male 42, 44 and 46 could be provided on the respective housing members 52 and 54 with the female bores or sockets 70, 72 and 74 provided on the housing member 36. In both cases, the principle of the present invention would be accomplished regardless of the positioning of the terminal pins or the female receptacle bores.

Referring to FIG. 12, an improved terminal socket member 28 is shown in combination with a medical electrode 6. The medical electrode 6 can, in a manner similar to that discussed with regard to the connector housing 36, accommodate a recessed terminal pin 76 which, as can be seen in FIG. 10, has the locking rim 50 intergraly provided as an extended shoulder. Additionally, the locking shoulder 78 and 80 can be provided on the upper and lower surfaces of the socket member 28 for frictional engagement with detent 82 and 84, respectively. As can be seen in the cross sectional view of FIG. 10, the locking rim 50 of the terminal pin is passing through the locking ring 60. The insulated housing connector 29 has a central bore that supports electrical conductive receptacle material 79 which will establish a conductive path with the terminal pin 76.

Figure 13:
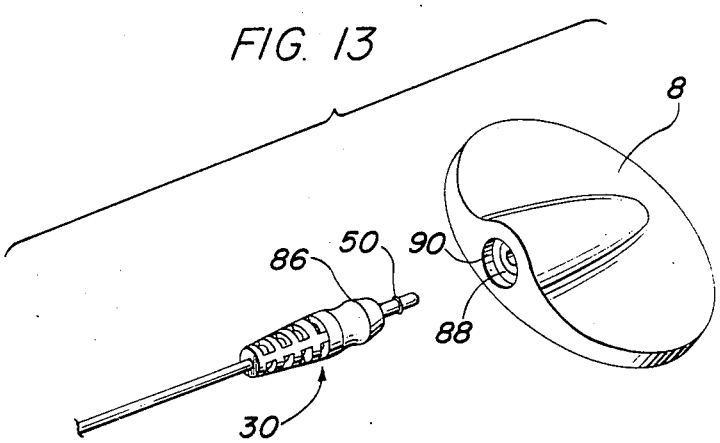
FIG. 13 is a perspective view of another electrode connector unit.

Referring to FIG. 13, an alternative configuration of an electrode is disclosed as electrode 8 for interfacing with the terminal jack 30. Again the terminal pin can have a locking rim 50 and additionally, molded on the housing 30, a locking annular shoulder 86 for interfacing with an annular detent 88 positioned within the entrance bore 90 of the electrode 8.

While the above embodiments have been disclosed as the best modes presently contemplated by the inventors, it should be realized that these examples should not be interpreted as limiting because artisans skilled in this medical field, once given the present teaching, can vary from the specific embodiments.

Accordingly, the scope of the present invention should be determined solely from the following claims in which we claim.

What is claimed is:

1. In a monitoring medical system for monitoring a physiological function of a patient including a transducer for providing electrical signals representative of a physiological function and a monitor for receiving electrical signals, the improvement of an electrical cable system comprising:
   a first cable unit having means for connection to a monitor, a first connector unit and a flexible electrical conduit interconnecting the connector with the monitor connection means;
   a second cable unit having a second connector unit, means for connection to a transducer and a second flexible electrical conduit interconnecting the second connector unit with the transducer connection means, one of the first and second connector units has a housing with a plurality of recesses and a plurality of tubular conductive terminal pins mounted entirely within the recesses, the other connector unit has a housing of a configuration to fit within a recess and has a conductive member with a terminal bore for receiving and establishing an electrical connection with a terminal pin, whereby a safety characteristic is provided to prevent connection of the transducer to an unauthorized electrical socket; and
   means for securing the first and second connector units together including a locking rim on the terminal pins of a larger diameter then the tubular configuration and a nonconductive thermoplastic annular locking ring mounted in the other connector unit before the terminal bore and having an opening of a lesser dimension than the locking rim and mounted to define an open space between the terminal bore of the conductive member and the locking ring to receive the locking rim.

2. The invention of claim 1 wherein the recesses have different perimeter configurations and the terminal bore housing configuration has a complimentary exterior configuration to insure a predetermined matching of a terminal pin and a terminal bore.

3. The invention of claim 1 wherein the means for connection to a transducer includes a square lead housing with an exterior locking rib.

4. The invention of claim 1 wherein the means for connection to a transducer includes a round lead housing with an exterior locking rib.

5. The invention of claim 1 wherein the second cable unit further includes a third connector unit, second means for connection to a transducer and a third flexible electrical conduit interconnecting the third connector unit with the second transducer connection means.

6. The invention of claim 5 wherein the second and third connector unit interlock with a detent provided on the exterior of one connector unit and a retaining lock member provided on the exterior of the other connector unit.

7. The invention of claim 6 wherein the housing of the first and second connector members are formed of a plastic material and the annular locking ring is formed of a relatively more rigid plastic material for interfacing with the metal terminal pins.

8. In a monitoring medical system for monitoring a physiological function of a patient including a transducer for providing electrical signals representative of a function and a monitor for receiving electrical signals, the improvement of an electrical cable system comprising:
   a first cable unit having means for connection to a monitor, a first connector unit and a flexible electrical conduit interconnecting the connector with the monitor connection means; and
   a second cable unit having a second connector unit, means for connection to a transducer and a second flexible electrical conduit interconnecting the second connector unit with the transducer connection means, one of the first and second connector units has a housing member with a plurality of recesses and a plurality of conductive terminal pins mounted entirely within the recesses in a cantilevered arrangement from the bottom of a recess, the other connector unit has a housing member of a configuration to fit within a recess and has a terminal bore for receiving and establishing an electrical connection with a terminal pin, the respective housing members are made of a flexible plastic material, the terminal pins have an elongated tubular configuration and integral with the tubular configuration at a position adjacent to and spaced from the bottom of a recess is a locking rim of a larger diameter than the tubular configuration, the terminal bore includes an annular non-conducting locking ring of a relatively rigid thermoplastic material compared to the housing members, with a central bore of a smaller diameter than the locking rim for receiving the locking rim in a snap fitting action to secure the terminal pin in the terminal bore and electrically conductive material for engaging the portion of the terminal pin forward of the locking rim, the annular locking ring includes a recessed annular shoulder and a spacing rim to define an open space between the electrically conductive material and the opening of the central bore of the locking ring.

9. The invention of claim 8 wherein the recesses have different perimeter configurations and the terminal bore housing configuration has a complimentary exterior configuration to insure a predetermined matching of a terminal pin and a terminal bore.

10. The invention of claim 8 wherein the means for connection to a transducer includes a square lead housing with a pair of exterior locking ribs.

11. The invention of claim 8 wherein the means for connection to a transducer includes a round lead housing with an exterior annular locking rib.

12. The invention of claim 8 wherein the second cable unit further includes a third connector unit, second means for connection to a transducer and a third flexible electrical conduit interconnecting the third connector unit with the second transducer connection means.

13. The invention of claim 12 wherein the second and third connector unit interlocking with a detent provided on the exterior of one connector unit and a stationary retaining lock member of a complimental configuration is provided on the exterior of the other connector unit.

14. A detachable safety lead medical cable assembly for interconnecting an accessory such as a transducer attached to a patient and a source of power such as a monitor, comprising:

a first cable unit having a first means for electrical connection to a source of power, a first intermediate connector unit and a flexible electrical conduit interconnecting the connector with the first means; and a second cable unit having a second means for electrical connection to an accessory, a second intermediate connector unit and a flexible electrical conduit interconnecting the connector with the second means, one of the first and second connector units has a housing with a recess and a plurality of terminal pins mounted within the housing in the recess, the other connector unit has a housing of a configuration to fit within the recess and has a pair of terminal bores for receiving and establishing electrical connection, respectively, with the terminal pins, one of the recess and the connector unit housing has an alignment member and the other has an alignment groove to define a predetermined detachable alignment configuration for the intermediate connectors; and means for securing the first and second connector units together including a locking rim on each terminal pin of a larger diameter than the configuration and a nonconductive thermoplastic annular locking ring mounted in the other connector unit before the terminal bore and having an opening of a lesser dimension than the locking rim and mounted to define an open space between the terminal bore of the conductive member and the locking ring to position the locking rim.

* * * * *